(12) United States Patent
Height et al.

(10) Patent No.: US 6,929,236 B1
(45) Date of Patent: Aug. 16, 2005

(54) APPARATUS FOR FLOW RATE CONTROL

(75) Inventors: Murray J. Height, Somerville, MA (US); Eun Young Hwang, Cambridge, MA (US); Timothy J. Prestero, Jamaica Plain, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/408,418

(22) Filed: Apr. 7, 2003

Related U.S. Application Data

(60) Provisional application No. 60/373,849, filed on Apr. 19, 2002, provisional application No. 60/374,662, filed on Apr. 23, 2002.

(51) Int. Cl.$^7$ ................................ F16K 7/04
(52) U.S. Cl. ........................... 251/6; 137/553
(58) Field of Search ............ 251/4, 6; 137/553

(56) References Cited

U.S. PATENT DOCUMENTS

| | | | |
|---|---|---|---|
| 1,959,074 A * | 5/1934 | Bloxsom | 251/6 |
| 2,444,767 A * | 7/1948 | Cobean | 251/6 |
| 2,595,511 A * | 5/1952 | Butler | 251/6 |
| 3,800,794 A | 4/1974 | Georgi | |
| 3,915,167 A * | 10/1975 | Waterman | 251/9 |
| 3,984,081 A * | 10/1976 | Hoganson | 251/6 |
| 4,037,598 A | 7/1977 | Georgi | |
| 4,061,700 A | 12/1977 | Gallivan | |
| 4,238,108 A | 12/1980 | Muetterties | |
| 4,261,388 A | 4/1981 | Shelton | |
| 4,270,725 A | 6/1981 | Scott et al. | |
| 4,337,791 A * | 7/1982 | Tech et al. | 251/6 |
| 4,338,932 A | 7/1982 | Georgi et al. | |
| 4,403,764 A * | 9/1983 | Repplinger | 251/6 |
| 4,452,273 A | 6/1984 | Hanzawa et al. | |
| 4,457,750 A | 7/1984 | Hill | |
| D280,763 S | 9/1985 | Kulle | |
| 4,585,442 A | 4/1986 | Mannes | |
| 4,601,700 A | 7/1986 | Thompson et al. | |
| 4,662,599 A | 5/1987 | Attermeier | |
| 4,802,506 A | 2/1989 | Aslanian | |
| 4,807,660 A | 2/1989 | Aslanian | |
| 4,869,721 A * | 9/1989 | Karpisek | 251/6 |
| 4,919,389 A | 4/1990 | Hoekwater et al. | |
| 4,974,811 A | 12/1990 | Ishida | |
| 5,045,069 A | 9/1991 | Imparato | |
| 5,190,079 A * | 3/1993 | Nakada | 251/6 |
| 5,259,587 A * | 11/1993 | D'Alessio | 251/4 |
| 5,718,409 A * | 2/1998 | Starchevich | 251/6 |
| 5,728,077 A | 3/1998 | Williams et al. | |
| 5,980,490 A | 11/1999 | Tsoukalis | |
| 6,129,330 A | 10/2000 | Guala | |
| 6,343,619 B1 * | 2/2002 | Pruitt | 137/556.6 |

* cited by examiner

*Primary Examiner*—John Bastianelli
(74) *Attorney, Agent, or Firm*—Daly, Crowley, Mofford & Durkee, LLP

(57) ABSTRACT

The apparatus for flow rate control of a fluid provides a roller clamp having either a clamp body with a non-linear clamp body surface or a clamp body with a non-linear adjustment roller track, which, when coupled to a tube, provides a linear, or otherwise pre-determined, relationship between flow rate of a fluid flowing through the tube and adjustment of the roller clamp.

22 Claims, 6 Drawing Sheets

APPARATUS FOR FLOW RATE CONTROL

CROSS REFERENCE TO RELATED APPLICATIONS

The present application claims the benefit under 35 U.S.C. §119(e) of U.S. Provisional Patent Application No. 60/373,849, filed on Apr. 19, 2002, and U.S. Provisional Patent Application No. 60/374,662, filed on Apr. 23, 2002, both of which are incorporated herein by reference.

STATEMENT REGARDING FEDERALLY SPONSORED RESEARCH

Not Applicable.

FIELD OF THE INVENTION

This invention relates generally to flow rate control devices and more particularly to devices that control the flow rate of a fluid flowing through a tube.

BACKGROUND OF THE INVENTION

As is known in the art, there are certain medical conditions which, if not treated, can lead to severe dehydration and death. Cholera is one example of such a medical condition. To treat cholera and other conditions, an intravenous (IV) drip infusion is often used to re-hydrate patients and/or to introduce medicine into a patient's body. An intravenous drip infusion of saline is the preferred technique for the medical treatment of severe cholera. In a cholera epidemic, where many patients need to be treated as quickly as possible, it is desirable set up IV equipment and initiate treatment as rapidly as possible.

As is also known in the art, a conventional IV drip set includes a fluid reservoir, a clear plastic drip chamber coupled to the fluid reservoir for visualization of fluid flow, a clear flexible tube coupled to the drip chamber, a roller clamp coupled to the flexible tube for flow rate control, and an attachment to connect the flexible tube to an intravenous catheter adapted to be placed into a patient. The roller clamp provides an adjustable force upon the flexible tube and therefore an adjustable flow restriction. The rate at which fluid flows through the tube is estimated by observing the drip rate in the drip chamber. The rate at which the fluid flows through the tube is adjusted by adjusting the roller clamp until the desired drip rate is achieved. Such conventional IV drip sets are simple, relatively inexpensive and find widespread use. One example of a conventional IV drip set is further described in conjunction with FIG. 1 below.

When using the IV drip set, it is important for the user to accurately regulate the flow of fluid (e.g. saline solution) into the patient. The roller clamp is used to adjust the flow rate of the fluid flowing through the flexible tube and therefore the flow rate into the catheter, which is inserted into the patient's body. A user turns an adjustment roller on the roller clamp to provide more or less force, or clamping action, upon the flexible tube and therefore more or less restriction of the flexible tube, thereby adjustably controlling the flow rate.

It is relatively difficult for a user to accurately adjust conventional roller clamps to accurately provide a specific flow rate. Thus, to arrive at a specific flow rate, it is often necessary to make an adjustment, observe the resultant flow rate via the drip chamber, and then re-adjust as necessary. These steps are repeated until arriving at a desired specific flow rate. Flow rate adjustment can, therefore, be a relatively time-consuming task.

The difficulty in adjusting the flow rate is due in part to a large non-linearity in flow rate control provided by conventional roller clamps. Essentially, as the user turns the adjustment roller of the conventional roller clamp, the flow rate is not linearly adjusted in proportion to the rotation of the adjustment roller. The non-linearity is sufficiently great that even a slight rotation of the adjustment roller in either direction can cause an undesired flow rate either higher or lower than the desired flow rate. Furthermore, with each adjustment of the adjustment roller, the drip rate in the drip chamber must be observed to determine the flow rate. Observation of the drip rate involves counting a number of drips over a time period, for example, 15 seconds. As described above, particularly in epidemic situations, it is necessary that set up of the IV drip set, including adjustment of the flow rate, be done quickly. Difficulty of flow rate adjustment slows the set up process.

Therefore, it would be desirable to provide a flow control apparatus that can be quickly adjusted to achieve a desired flow rate of a fluid flowing through a tube and into a catheter. It would be further desirable to provide a flow rate apparatus, which is relatively low cost and simple. It would also be desirable to provide a flow control apparatus that is manual and that requires no power supply.

SUMMARY OF THE INVENTION

In accordance with the present invention, an apparatus for flow rate control of fluid includes a clamp body having an adjustment roller track and a non-linear clamp body surface. An adjustment roller is coupled to the clamp body and is movable along the adjustment roller track such that a surface of the adjustment roller is spaced a distance from the non-linear clamp body surface. The distance is proportional to a location of the adjustment roller along the adjustment roller track. When coupled to a tube, the selected distance provides a selected force upon the tube and therefore a selected restriction in the tube. The selected restriction provides a selected flow rate of the fluid flowing through the tube.

With this particular arrangement, the apparatus provides an adjustment of the flow rate of the fluid flowing through the tube that has a predetermined relationship between flow rate and rotation of the adjustment roller. In the one particular embodiment, the relationship is substantially linear so that the number of degrees of rotation of the adjustment roller is substantially linearly proportional to the flow rate.

In accordance with another aspect of the present invention, an apparatus for flow rate control of a fluid includes a clamp body having a non-linear adjustment roller track and a clamp body surface. An adjustment roller is coupled to the clamp body and is movable along the non-linear adjustment track such that a surface of the adjustment roller is spaced a distance from the clamp body surface. The distance is proportional to a location of the adjustment roller along the adjustment roller track. When attached to a tube, the selected distance provides a selected force upon the tube and therefore a selected restriction in the tube. The selected restriction provides a selected flow rate of the fluid flowing through the tube.

With this particular arrangement, the apparatus provides an adjustment of the flow rate of the fluid in the tube that has a predetermined relationship between flow rate and rotation of the adjustment roller. In the one particular embodiment, the relationship is essentially linear so that the number of degrees of rotation of the adjustment roller is essentially linearly proportional to the flow rate. A user can easily set the flow rate.

In accordance with another aspect of the present invention, an apparatus for flow rate control of a fluid includes a clamp body having an adjustment roller track and a clamp body surface. An adjustment roller is coupled to the clamp body and is movable along the adjustment roller track such that a surface of the adjustment roller is spaced a distance from the clamp body surface. The distance is proportional to a location of the adjustment roller along the adjustment roller track. The apparatus also includes an adjustment scale disposed on a surface of the clamp body. In one particular embodiment, the scale is a linear scale that indicates the location of the adjustment roller along the adjustment roller track, and therefore, the flow rate of the fluid flowing through the tube.

With this particular arrangement, the apparatus for flow rate control provides the user with the ability to rapidly set up and control the flow rate of the fluid. Having a visual scale corresponding to the location of the adjustment roller allows the user to rapidly set the apparatus to a known flow rate.

BRIEF DESCRIPTION OF THE DRAWINGS

The foregoing features of the invention, as well as the invention itself may be more fully understood from the following detailed description of the drawings, in which.

DETAILED DESCRIPTION OF THE INVENTION

Figure 1:
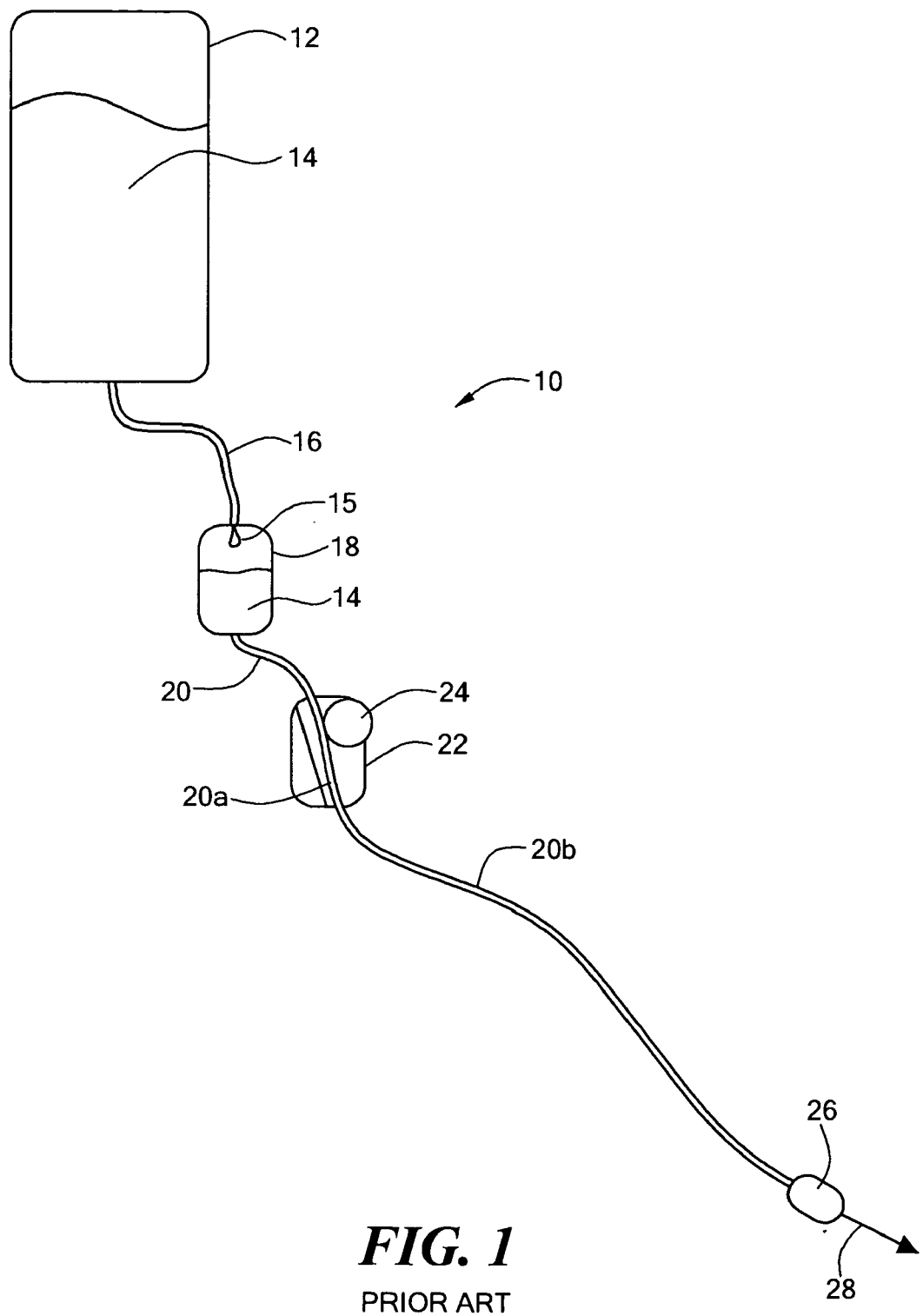
FIG. 1 is a pictorial of a prior art IV drip apparatus.

Referring now to FIG. 1, a prior art intravenous (IV) drip set 10 includes a fluid reservoir 12 containing a fluid 14. The fluid reservoir 12 can be provided, for example, as a conventional fluid bag (e.g., saline or blood) or as any other type of fluid container. The IV drip set 10 also includes a drip chamber 18 coupled to the fluid reservoir 12 with a tube 16. The drip chamber 18 allows a user to view the flow rate of the fluid 14a flowing in the tube 16 by viewing a drip rate of falling drops 15. The fluid 14 flows out of the drip chamber 18 and into a tube 20 having tube portions 20a and 20b. The tube 20 can be one of a variety of compressible tubes. For example, in one particular embodiment, the tube 20 is a flexible plastic tube. A roller clamp 22 having an adjustment roller 24 is coupled to the tube portion 20a. The tube portion 20b is coupled with an attachment 26 to a catheter 28, which is inserted into a patient (or an animal).

The prior art roller clamp 22 is described in detail in conjunction with FIG. 2 below. Suffice it here to say that, in operation, the roller clamp 22 provides a variable force, and therefore, a variable compression, upon the tube portion 20a, in proportion to manual rotation of the adjustment roller 24 by a user. The variable compression provides a selectable restriction of the tube portion 20b. Therefore, by observing the rate of drops 15 falling in the drip chamber 18, and turning the adjustment roller 24 in order to select a drip rate, a user selects a flow rate of the fluid 14 flowing through the tube 20 and into the arm of the patient.

Figure 2:
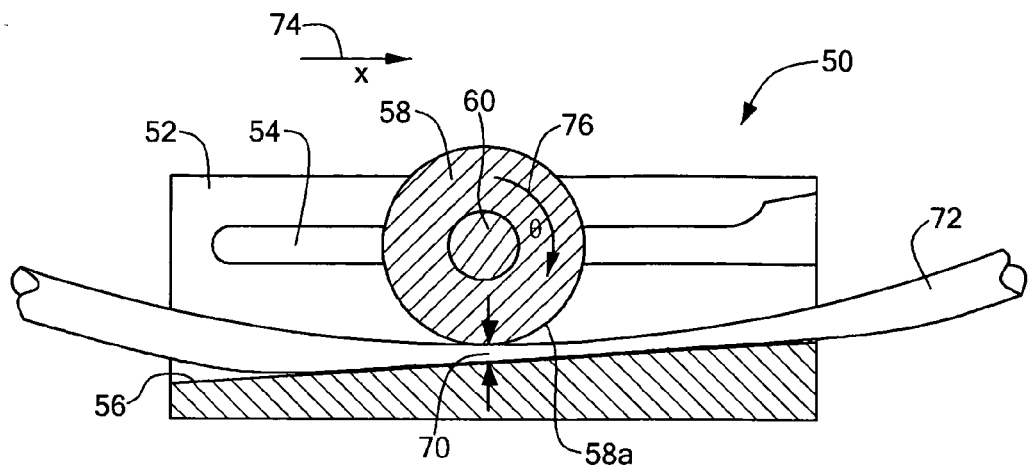
FIG. 2 is a cross-sectional view of a prior art roller clamp coupled to a tube.

Referring now to FIG. 2, an exemplary prior art roller clamp 50, shown in a cross-sectional view, includes a clamp body 52, having an adjustment roller track 54 and a clamp body surface 56. An adjustment roller 58 is coupled to the clamp body 52 by way of an axle 60 that can move along the adjustment roller track 54. The adjustment roller track 54 of the prior art roller clamp 50 is substantially linear. The clamp body surface 56 of the prior art roller clamp 50 is also substantially linear, i.e., the adjustment roller track 54 has a planar surface in an x-direction 74 in which the adjustment roller 58 can move along the adjustment roller track 54. The clamp body surface 56 is at a substantially constant angle relative to the adjustment roller track 54.

The roller clamp 50 is adapted to couple to a tube 72, such that the tube 72 is disposed between a surface 58a of the adjustment roller 58 and the clamp body surface 56. The tube 72 can correspond, for example, to the tube portion 20a of FIG. 1. When the user turns the adjustment roller 58, the adjustment roller 58, having friction against the tube 72, moves along the tube 72, thereby moving along the adjustment roller track 54. As the adjustment roller 58 is turned, moving along the adjustment roller track 54, the clamp body 52 remains substantially stationery relative to the tube 72.

A variable gap 70 between the adjustment roller surface 58a and the clamp body surface 56 has a size proportional to the location of the adjustment roller 58 along the adjustment roller track 54. Turning the adjustment roller 58 in a clockwise direction 76 tends to move the adjustment roller 58 in the x-direction 74. Since the clamp body surface 56 is at an angle with respect to the adjustment roller track 54, the width of the variable gap 70 decreases as the adjustment roller 58 turns in a clockwise direction (i.e., toward the right of FIG. 2). Conversely, the width of the variable gap 70 increases as the adjustment roller 58 turns in a counterclockwise direction (i.e., toward the left in FIG. 2). Reducing the size of the variable gap 70 causes the tube 72, disposed into the variable gap 70, to compress by a greater amount, thereby decreasing flow rate of a fluid flowing through the tube 72.

The conventional roller clamp 50 provides a very non-linear relationship between the position (i.e., the rotation) of the adjustment roller 58 and the flow rate. At some flow rate settings, even a slight rotation of the adjustment roller in either direction can cause the flow rate to be outside of desired bounds.

Figure 3:
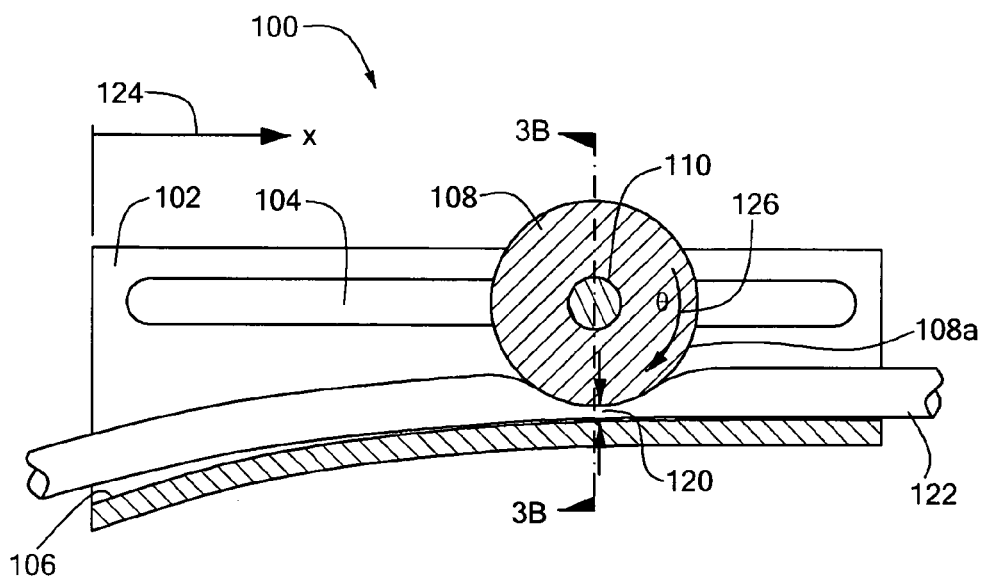
FIG. 3 is a cross-sectional view of an exemplary roller clamp in accordance with the present invention coupled to a tube.

Referring now to FIG. 3, an exemplary roller clamp 100 in accordance with the present invention, shown in a cross-sectional view, includes a clamp body 102 having an adjustment roller track 104 and a non-linear clamp body surface 106. An adjustment roller 108 is coupled to the clamp body 102 by way of an axle 110 that can move along the adjustment roller track 104. Other techniques may of course be used to movably couple the adjustment roller 108 to the clamp body 102. The adjustment roller track 104 is substantially linear. However, the non-linear clamp body surface 106 is non-linear along an x-direction 124 in which the adjustment roller 108 can move along the adjustment roller track 104.

The roller clamp 100 is adapted to couple to a tube 122, such that the tube 122 is disposed between a surface 108a of the adjustment roller 108 and the clamp body surface 106. The tube 122 can correspond, for example, to the tube portion 20a of FIG. 1. When the user turns the adjustment roller 108, the adjustment roller 108, having function against the tube 122, moves along the along the tube 122, thereby moving along the adjustment roller track 104.

A variable gap 120 between the adjustment roller surface 108a and the non-linear clamp body surface 106 has a size proportional to the location of the adjustment roller 108 along the adjustment roller track 104. Turning the adjustment roller 108 in a clockwise-direction 126 tends to move the adjustment roller 108 in the x-direction 124 (i.e. towards the right in FIG. 3), therefore reducing the size of the variable gap 120. Reducing the size of the variable gap 120 causes the tube 122, disposed into the variable gap 120, to compress by a greater amount, thereby decreasing flow rate through the tube 122.

The exemplary roller clamp 100 provides a predetermined relationship between the location (i.e., the rotation) of the adjustment roller 108 and the flow rate. The relationship is associated with a predetermined curvature of the non-linear clamp body surface 106. In one particular embodiment, the curvature of the non-linear clamp body surface 106 is selected so that the relationship between the location of the adjustment roller and the flow rate is essentially linear. With this particular arrangement, the flow rate setting is quickly and easily achieved throughout a substantial portion of the range of adjustment roller locations.

In another embodiment, the curvature of the non-linear clamp body surface 106 is selected so that the relationship between the location of the adjustment roller and the flow rate has a predetermined non-linearity. For example, at low flow rates, it may be desirable to have a decreased sensitivity to rotation of the adjustment roller clamp 58. Therefore, in one particular embodiment, the curvature of the non-linear adjustment roller track 122 is selected so that at low flow rates the user must turn the adjustment roller 108 by a greater amount to change the flow rate than required at high flow rates.

The relationship between the location of the adjustment roller 108 and the flow rate is determined by a variety of factors in addition to the curvature of the non-linear clamp body surface 106. Other factors that influence the relationship include, but are not limited to, the outer diameter of the tube 122, the inner diameter of the tube 122, and the type of fluid flowing through the tube 122. The fluid flowing through the tube 122 can be can be a liquid, a gas, or a mixed phase combination of any of a liquid, a gas, and solids.

It should be appreciated that surface 106 may be provided as a relatively smooth surface or as a stepped surface. When surface 106 is provided as a smooth surface, the roller may be moved in a continuous fashion to provide continuously variable or analog control. When surface 106 is provided as a stepped surface, the roller 108 may be moved from one step to the next to provide incremental control (or digital-like control).

Figure 3A:
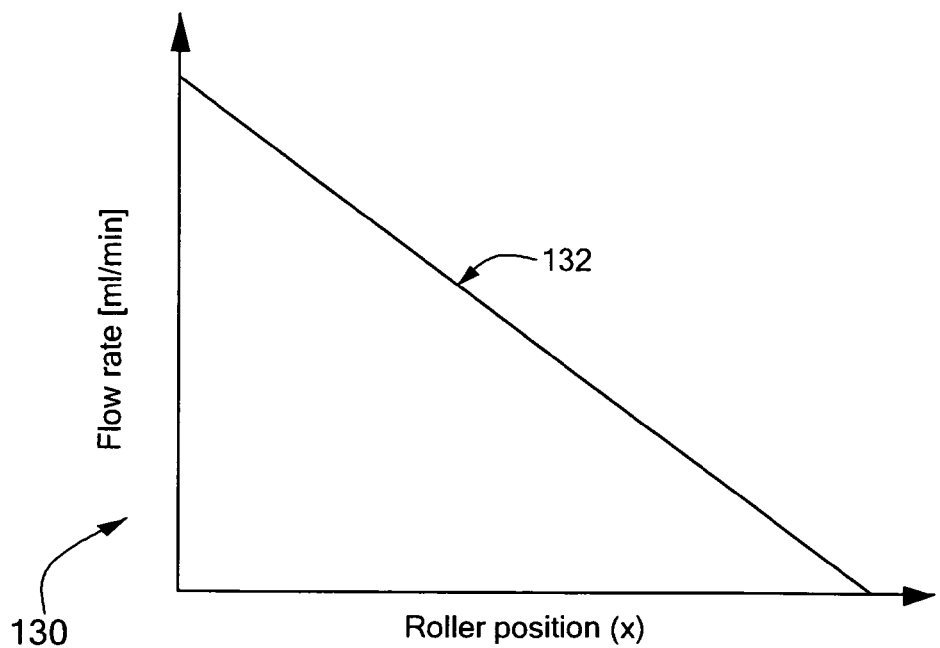
FIG. 3A is a plot of flow rate vs. roller position for the exemplary roller clamp of FIG. 3.

Referring now to FIG. 3A, a graph 130 of flow rate through a tube (e.g., 122, FIG. 3) versus adjustment roller location includes a vertical axis corresponding to flow rate having units of flow in mL/min and a horizontal axis corresponding to location of the adjustment roller (e.g., 108, FIG. 3) along the adjustment roller track (e.g., 104, FIG. 3) in the x-direction (e.g., 124, FIG. 3) having units of distance in millimeters. A curve 132 illustrates to the relationship between the location of the adjustment roller (e.g., roller 108, FIG. 3) and the flow rate. It can be seen that the flow rate has an essentially linear relationship with respect to the location of the adjustment roller.

As described in conjunction with FIG. 3, while a linear relationship is shown by the curve 132, other relationships can also be provided by the roller clamp in accordance with the present invention by selecting a non-linear clamp body surface (e.g., 106, FIG. 3) having another curved shape.

Figure 3B:
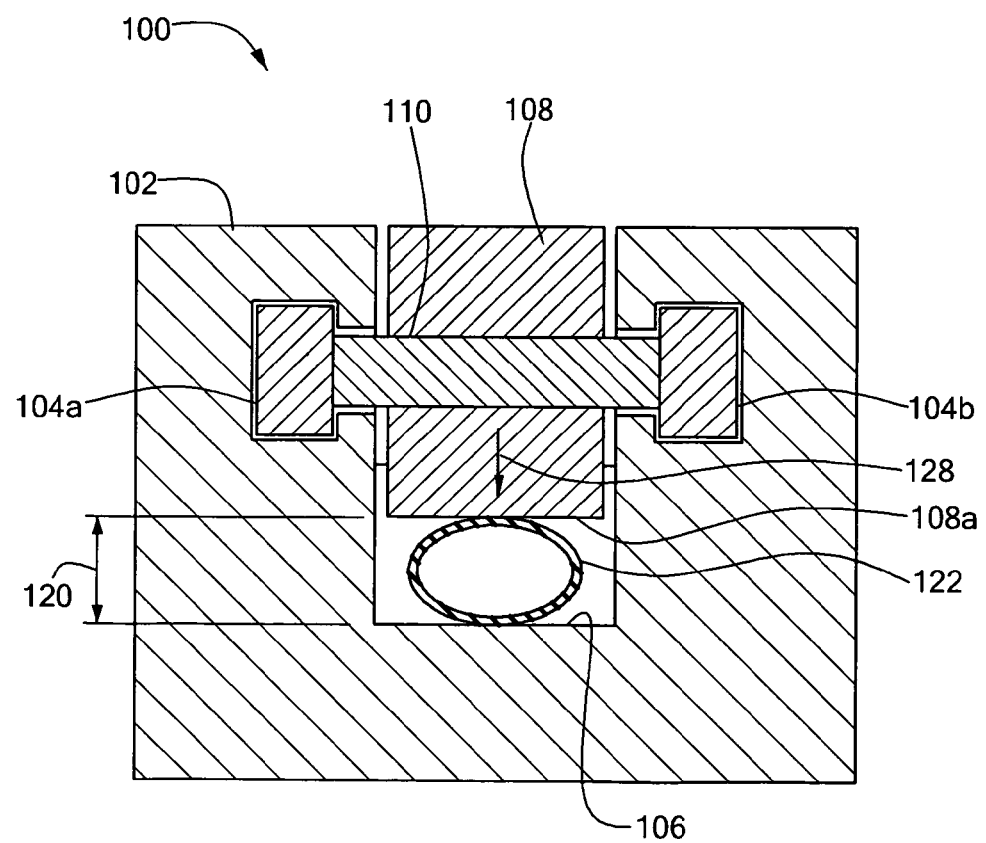
FIG. 3B is a cross-sectional view of the roller clamp FIG. 3 taken along line 3B—3B of FIG. 3.

Referring now to FIG. 3B, in which like elements o FIG. 3 are shown having like reference designations, the roller clamp 100 of FIG. 3 is shown in a cross-sectional view taken along line 3B—3B of FIG. 3. The tube 122 is in compression between the non-linear clamp body surface 106 and the surface 108a of the adjustment roller 108. The tube 122, which would otherwise have a round cross section, is temporarily deformed by the compression provided by the adjustment roller 108 and the non-linear clamp body surface 106.

As the adjustment roller 108 is rotated by a user in the clockwise-direction 124 (FIG. 3), and therefore moved along the adjustment roller track 104 in the x-direction 124 (FIG. 3), the variable gap 120 between the adjustment roller surface 108a and the non-linear clamp body surface 106 becomes smaller, increasing the compression of the tube 122, and further reducing flow through the tube 122. When the adjustment roller 108 is rotated in the opposite direction by a user (i.e. in the counter-clockwise direction), the variable gap 120 becomes larger, decreasing the compression of the tube. When the compression of the tube 122 is decreased, the tube 122 relaxes to a less compressed shape, and the flow through the tube increases accordingly.

The adjustment roller 108 provides an adjustable compressive force 128 upon the tube 122 as the adjustment roller 108 moves along the adjustment roller track 104 in response to rotation of the adjustment roller 108. By selectively compressing the tube 122, and therefore selectively changing the cross sectional area of the tube 122, the flow rate through the tube 122 is controlled as a function of location of the adjustment roller 108 along the adjustment roller track 104. As described above, it should be recognized that the location of the adjustment roller 108 along the adjustment roller track 104 is a function of the degrees of rotation of the adjustment roller 108.

Figure 4:
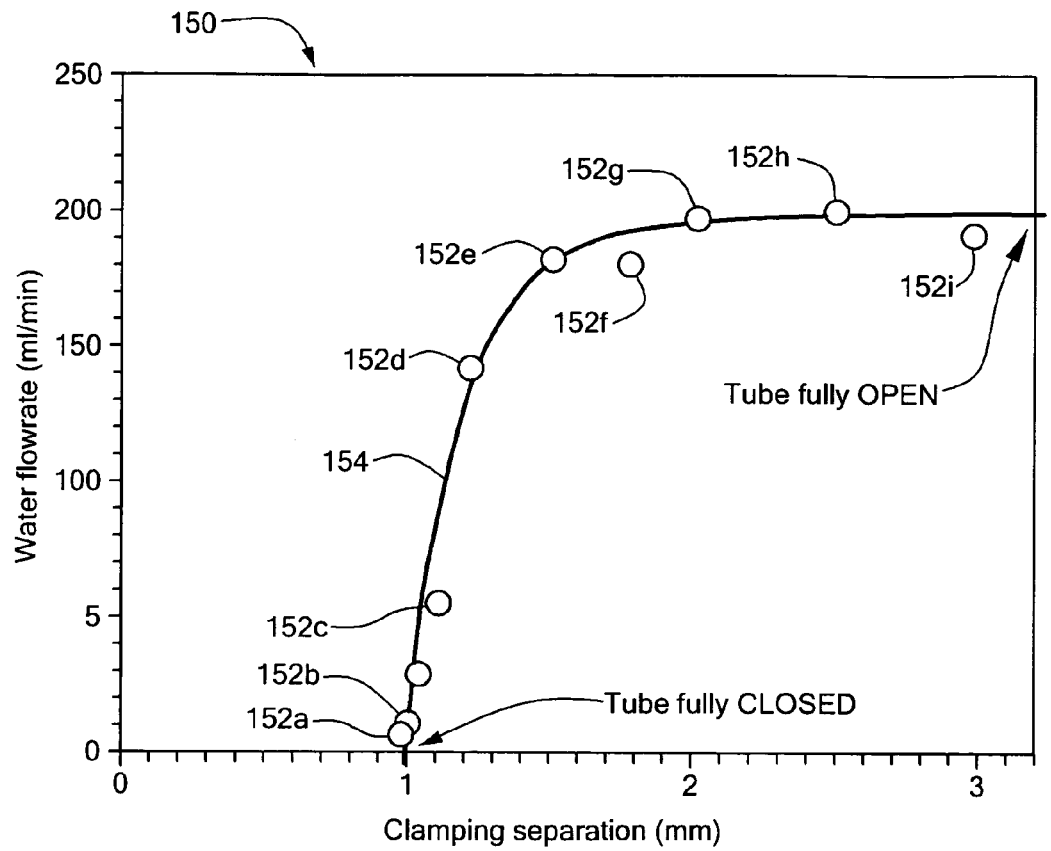
FIG. 4 is a plot of water flow rate vs. clamping separation.

Referring now to FIG. 4, a graph 150 showing empirical flow rate data has a vertical scale in units of milliliters per minute corresponding to flow rate through a tube (e.g., tube 122, FIG. 3) and a horizontal scale in units of millimeters corresponding to "clamping separation." The clamping separation is understood to be the dimension of the variable gap 120 of FIG. 3. A curve 154 is a best-fit curve through a plurality of data points 152A–152F. As can be seen by the curve 154, the flow rate is a non-linear function of the clamping separation.

The curve 154 can be described by the following equation:

$$Q = a(1 - D^{-b})$$

In the above equation, Q is the flow rate (mL/minute), and D is the clamping separation (mm). The constants, a and b, correspond to a particular tube (e.g., 122, FIG. 3) having a particular inner and outer diameter. In one particular arrangement, a is equal to 198.9 and b is equal to 5.9, corresponding to a tube having an inner diameter of two millimeters, an outer diameter of three millimeters, and a wall thickness of 0.5 millimeters.

In accordance with the present invention, the non-linear clamp body surface (e.g., 106, FIG. 3) has a shape selected to be in compliment with the non-linear flow rate shown by the curve 154. Essentially, the non-linear clamp body surface (e.g., 106, FIG. 3) of the present invention has a shape that provides an essentially linear relationship between the flow rate through the tube (e.g. 122, FIG. 3) and the location (i.e. the rotation) of the adjustment roller (e.g., 108, FIG. 3), in spite of the non-linear relationship between clamping separation and flow rate shown by the curve 154.

While the graph 150 corresponds to a particular tube having particular dimensions and to a particular non-linear function, one of ordinary skill in the art will recognize that other tubes having other dimensions have different non-linear relationships between flow rate and clamping separation.

Figure 5:
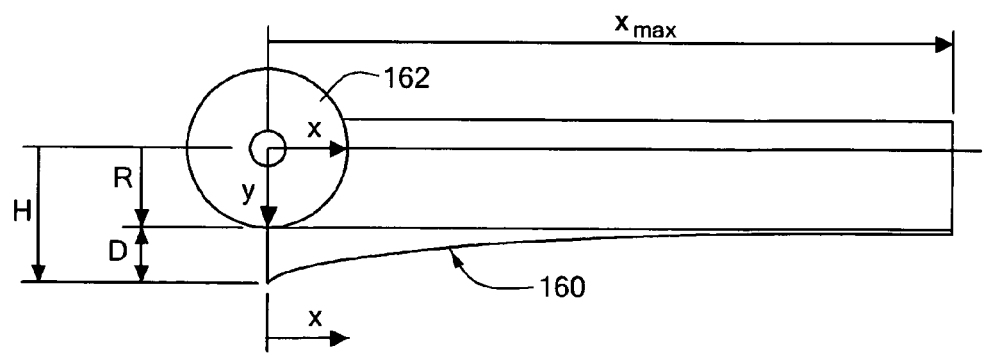
FIG. 5 is a view of a curved profile associated with a clamp body surface in accordance with the present invention.

Referring now to FIG. 5, in one exemplary embodiment, a curved profile 160 corresponding to a particular non-linear clamp body surface (e.g., surface 106, FIG. 3) can be determined by examining the curve 154 shown in FIG. 4.

The following equation describes a linear relationship between flow rate, Q, and roller location, x, where the location, x, corresponds to that x-direction 124 of FIG. 3.

$$Q = -Mx + B$$

In the above equation, the slope is given by $M = Q_{max}/x_{max}$ and intercept by $B = Q_{max}$.

Here, $Q_{max}$ is the maximum flow rate when the tube is fully open and $x_{max}$ is the length of the non-linear clamp body surface (e.g., 106, FIG. 3).

Rearranging and combining the above two equations yields:

$$D = (1 - Q/a)^{-1/b}$$

Substituting for Q gives:

$$D = (1 + Q_{max}/a(x/x_{max} - 1))^{-1/b}$$

It will be recognized that H=R+D where R is the radius of the adjustment roller 162. Substitution yields the following resulting equation that describes the shape of the curved profile 160.

$$H = (1 + Q_{max}/a(x/x_{max} - 1))^{-1/b} + R$$

Figure 6:
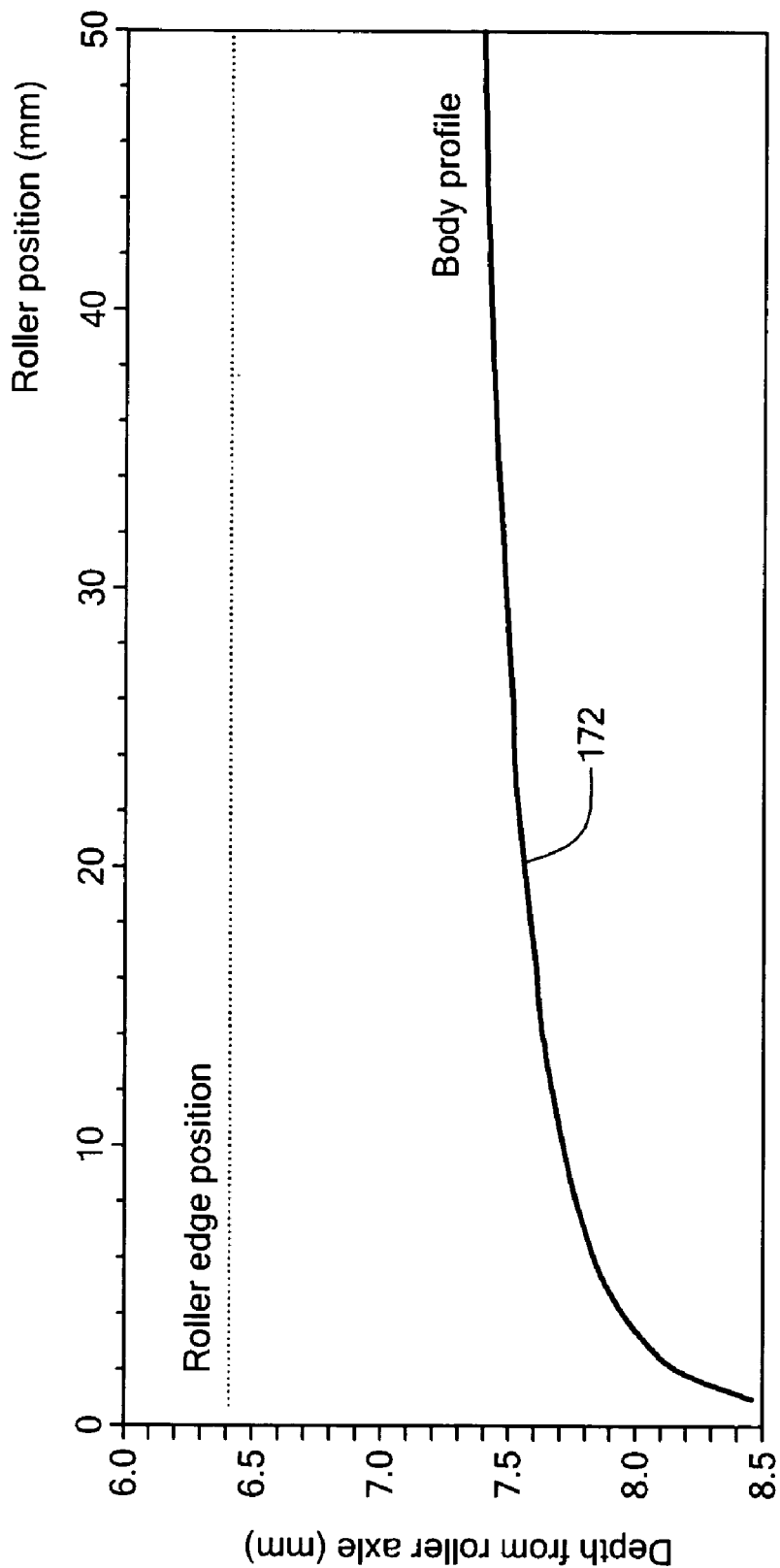
FIG. 6 is a plot showing a curved profile associated with a clamp body surface in accordance with the present invention.

Referring now to FIG. 6, a graph 170 has a vertical scale in millimeters corresponding to distance between the non-linear clamp body surface (e.g., 106, FIG. 3) and the axis of the adjustment roller axle (e.g., 110, FIG. 3), and a horizontal scale in millimeters corresponding to distance along the clamp body (e.g., 124, FIG. 3). A curve 172, also referred to as a curved profile 172, corresponds to the shape of the non-linear clamp body surface, for example the non-linear clamp body surface 106 shown in FIG. 3.

The curved profile 172 corresponds to one particular embodiment, in which the above equation for H is applied to yield the non-linear clamp body surface that provides an essentially linear flow rate proportional to the location of the adjustment roller (e.g., 108, FIG. 3), and wherein $Q_{max}=200$ mL/min, $X_{max}=50$ mm, R=6.4 mm, a=198.9, and b=5.9.

It should be recognized that the curved profile 172 corresponds to a calculated non-linear clamp body surface corresponding to particular empirical data, for example the empirical flow rate data of FIG. 4. The curved profile also corresponds to particular empirical constants, a and b, given above. Therefore, other empirical data and other empirical constants, corresponding, for example, a tube having other flow rate characteristics, can result in a different curved profile.

While one particular non-linear clamp body surface shape 172 is shown, with which an essentially linear flow rate control is achieved, it should be recognized that other non-linear clamp body surfaces can be provided in accordance with other tubes having other diameters or having other flow characteristics. Other non-linear clamp body surfaces can also be provided in accordance with liquids having other viscosities and other flow characteristics.

Furthermore, though the non-linear clamp body surface has been shown and described to provide a flow rate having an essentially linear relationship to rotation of the adjustment roller (e.g., 108, FIG. 3), other non-linear clamp body surfaces can be provided by this invention to provide other flow rate relationships. For example, as described above, it may be desirable to provide a non-linear clamp body surface that provides flow rate control that is less sensitive to adjustment roller location at low flow rates, and more sensitive at high flow rates. This invention is not limited to only those non-linear clamp body surfaces that provide an essentially linear relationship between flow rate and adjustment roller location.

Figure 7:
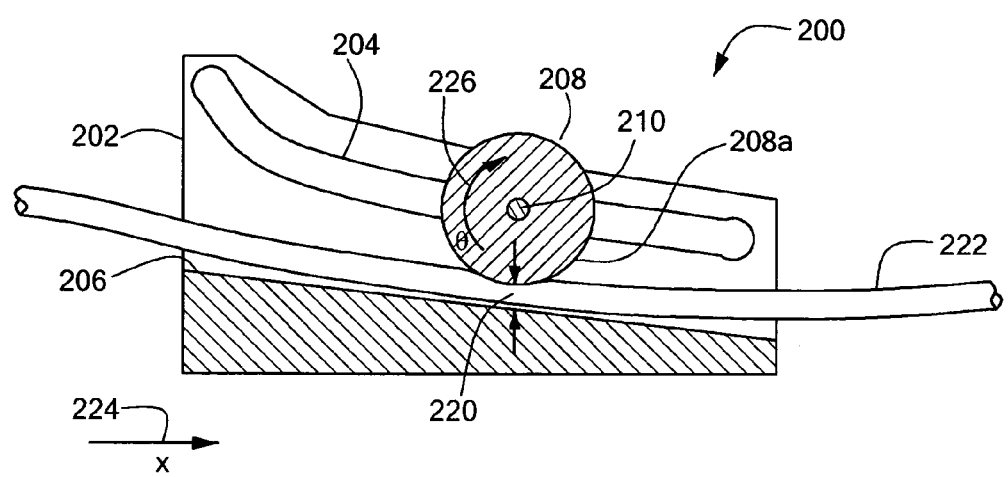
FIG. 7 is a cross-sectional view of an alternate embodiment of a roller clamp in accordance with the present invention.

Referring now to FIG. 7, an alternate embodiment of a roller clamp 200 in accordance with the present invention also provides an essentially linear, or otherwise predetermined, relationship, between flow rate of fluid flowing though a tube and location of an adjustment roller 208. The roller clamp 200, shown in a cross sectional view, includes a clamp body 202 having a non-linear adjustment roller track 204, a linear clamp body surface 206, and an adjustment roller 208 moveably coupled to the clamp body 202 via an axle 210. The adjustment roller 208 can be turned and the adjustment roller 208 can move along the non-linear adjustment roller track 204 in much the same way as described above for the roller clamp 100 of FIG. 3.

The roller clamp 200 is adapted to couple to a tube 222. In response to turning the adjustment roller 208, the adjustment roller, having friction against the tube 222, moves along the non-linear adjustment roller track 204.

A variable gap 220 between the adjustment roller surface 208a and the clamp body surface 206 has a size proportional to the location of the adjustment roller 208 along the adjustment roller track 204. Turning the adjustment roller 208 in a clockwise-direction 226 tends to move the adjustment roller 208 in an x-direction 224 (i.e., towards the right in FIG. 7), therefore reducing the size of the variable gap 220. Reducing the size of the variable gap 220 causes the tube 222, disposed into the variable gap 220, to compress by a greater amount, thereby decreasing flow rate of a fluid flowing through the tube 222.

The exemplary roller clamp 200 provides a predetermined relationship between the location (i.e., the rotation) of the adjustment roller 208 and the flow rate. A curvature or the non-linear adjustment roller track 204 provides the relationship, in a way similar to the curvature of the non-linear clamp body surface 106 of FIG. 3 described above.

In one particular embodiment, the curvature of the non-linear adjustment roller track 204 is selected so that the relationship between the location of the adjustment roller 208 and the flow rate is essentially linear. Essentially, the shape of the non-linear adjustment roller track 204 is provided in compliment to the non-linear flow rate provided by force upon the tube (see FIG. 4). With this particular arrangement, the flow rate setting is easily achieved throughout a substantial portion of the range of adjustment roller locations.

In another embodiment, the curvature of the non-linear adjustment roller track 204 is selected so that the relationship between the location of the adjustment roller 208 and the flow rate has a pre-determined non-linearity. For example, at low flow rates, it may be desirable to have a decreased sensitivity to rotation of the adjustment roller clamp 208 as described above in conjunction with FIG. 3.

The relationship between the location of the adjustment roller 208 and the flow rate is determined by a variety of factors in addition to the curvature of the non-linear adjustment roller track 204. Other factors that influence this relationship include, but are not limited to the outer diameter of the tube 222, the inner diameter of the tube 222, and the type of fluid flowing through the tube 222.

In other embodiments, aspects of the roller clamp 100 of FIG. 3 and the roller clamp 200 of FIG. 7 can be combined. For example, a combined clamp can include both a non-linear adjustment roller track and a non-linear clamp body surface.

While the roller clamps 100, 200 of FIGS. 3 and 7 respectively have been described as applied to an IV drip system, it should be appreciated that the roller clamps 100, 200 can be applied to a variety of applications for which flow rate control can be provided by force, or clamping action, upon a tube. For examples, the roller clamps 100, 200 can be applied to each of the following: a control valve for slurries, pastes and suspensions; a laboratory fluid control; and a gas flow rate control.

Figure 8:
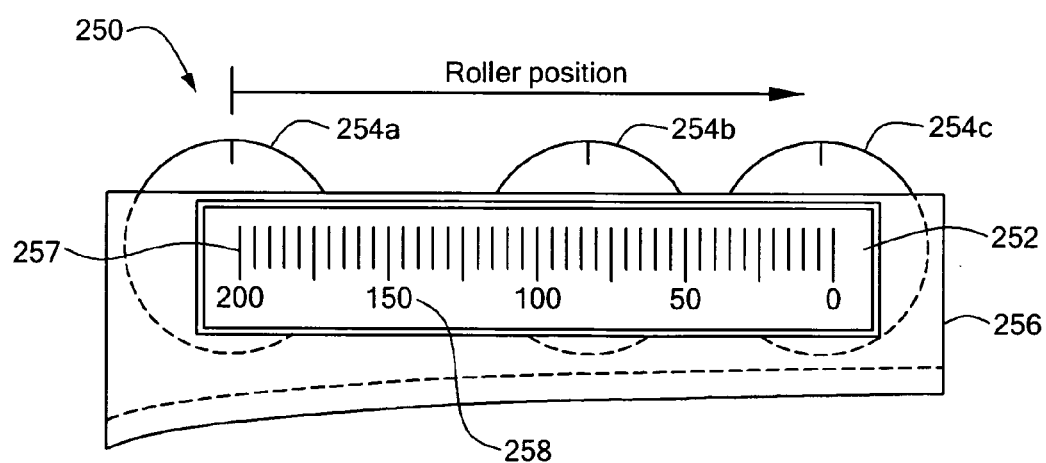
FIG. 8 is a view of a roller clamp scale in accordance with the present invention.

Referring now to FIG. 8, an exemplary roller clamp 250 includes a scale 252 that indicates a location of an adjustment roller 254, here shown in three locations 254a–254c. The scale 252, for example, can be can be applied to the roller clamps 100, 200 of FIGS. 3 and 7 respectively, and in particular to the respective roller clamp bodies 102, 202. As described above, in particular embodiments of the roller clamps 100, 200, the flow rate is essentially linearly proportional to location of the adjustment roller (108, 208, FIGS. 3, 7 respectively). Therefore, in those linear embodiments, the scale 252 can have linear graduations 254. However, the scale can also be applied to the conventional roller clamp of FIG. 2.

The scale 252 can be permanently affixed to the roller clamp 250, for example as a scale 250 molded into the roller clamp body 252. In an alternate embodiment, the scale can be affixed to the roller clamp 250 with tape, adhesive, or the like.

The scale 252 provides a visual indication of location of the adjustment roller 254, and therefore, a visual indication of the flow rate through a tube (not shown) to which the roller clamp 250 is coupled. The user can therefore rapidly and accurately move the adjustment roller 254 to a desired location relative to the scale 252 to set a desired flow rate. The scale can have graduations 257 with or without associated numerical labels 258. The numerical labels 258 can represent flow rate in desired units, for example in mL/min or in drops per minute, equivalent to the drip chamber (e.g., 18, FIG. 1), or in any other units corresponding to flow rate.

All references cited herein are hereby incorporated herein by reference in their entirety.

Having described preferred embodiments of the invention, it will now become apparent to one of ordinary skill in the art that other embodiments incorporating their concepts may be used. It is felt therefore that these embodiments should not be limited to disclosed embodiments, but rather should be limited only by the spirit and scope of the appended claims.

What is claimed is:

1. An apparatus for control of the flow rate of a fluid, comprising:
   a clamp body having an adjustment roller track and a non-linear clamp body surface, wherein the non-linear clamp body surface has a continuous curve throughout a substantial portion of a length of the clamp body surface; and
   an adjustment roller coupled to said clamp body and moveable along the adjustment roller track such that a surface of said adjustment roller is spaced a distance from the non-linear clamp body surface.

2. The apparatus of claim 1, wherein the distance between the surface of said adjustment roller and the non-linear clamp body surface is proportional to the location of the adjustment roller along the adjustment roller tack.

3. The apparatus of claim 1, wherein the non-linear clamp body surface and the surface of said adjustment roller are adapted to contact a tube.

4. The apparatus of claim 3, wherein said adjustment roller can be rotated to generate a selected force upon the tube, and wherein the control of the flow rate of the fluid in the tube is substantially linearly proportional to rotation of said adjustment roller throughout a substantial rotation of said adjustment roller.

5. The apparatus of claim 1, wherein said clamp body includes an adjustment scale which, relative to a position of the adjustment roller, indicates a flow rate value corresponding to the flow rate of the fluid.

6. The apparatus of claim 5, wherein said adjustment scale has a linear scale.

7. The apparatus of claim 5, wherein said adjustment scale has a non-linear scale.

8. The apparatus of claim 5, wherein said adjustment scale is molded into a surface of said clamp body.

9. The apparatus of claim 5, wherein said adjustment scale comprises an adhesive sheet conjoined with a surface of said clamp body.

10. The apparatus of claim 1, wherein the flow rate of the fluid is substantially linearly proportional to the rotation of said adjustment roller throughout a substantial rotation of said adjustment roller.

11. The apparatus of claim 1, wherein the fluid is saline solution used in an intravenous drip set.

12. An apparatus for control of the flow rate of a fluid, comprising:
   a clamp body having a non-linear adjustment roller track and a clamp body surface, wherein the non-linear adjustment roller track has a continuous curve throughout a substantial portion of a length of the non-linear adjustment roller track; and
   an adjustment roller coupled to said clamp body and moveable along the non-linear adjustment roller track such that a surface of said adjustment roller is spaced a distance from the clamp body surface.

13. The apparatus of claim 12, wherein the distance between the surface of said adjustment roller and the clamp body surface is proportional to the location of the adjustment roller along the adjustment roller track.

14. The apparatus of claim 12, wherein the clamp body surface and the surface of said adjustment roller are adapted to contact a tube.

15. The apparatus of claim 14, wherein said adjustment roller can be rotated to generate a selected force upon the tube, and wherein the flow rate of the fluid in the tube is substantially linearly proportion to rotation of said adjustment roller throughout a substantial rotation of said adjustment roller.

16. The apparatus of claim 12, wherein said clamp body includes an adjustment scale which indicates a flow rate value corresponding to the flow rate of the fluid.

17. The apparatus of claim 16, wherein said adjustment scale has a linear scale.

18. The apparatus of claim 16, wherein said adjustment scale has a non-linear scale.

19. The apparatus of claim 16, wherein said adjustment scale is molded into a surface of said clamp body.

20. The apparatus of claim 16, wherein said adjustment scale comprises an adhesive sheet conjoined with a surface of said clamp body.

21. The apparatus of claim 12, wherein the flow rate of the fluid is substantially linearly proportional to the rotation of said adjustment roller throughout a substantial rotation of said adjustment roller.

22. The apparatus of claim 12, wherein the fluid is saline solution used in an intravenous drip set.

* * * * *

UNITED STATES PATENT AND TRADEMARK OFFICE
CERTIFICATE OF CORRECTION

PATENT NO. : 6,929,236 B1
DATED : August 16, 2005
INVENTOR(S) : Murray J. Height et al.

It is certified that error appears in the above-identified patent and that said Letters Patent is hereby corrected as shown below:

Column 5,
Line 14, delete "moves along the along the" and replace with -- moves along the --.
Line 56, delete "can be can be a" and replace with -- can be a --.

Column 6,
Line 3, delete "to location" and replace with -- to the location --.
Lines 16-17, delete "o FIG. 3" and replace with -- of FIG. 3 --.

Column 8,
Line 35, delete "though a tube" and replace with -- through a tube --.

Column 9,
Line 32, delete "For examples," and replace with -- For example, --.
Line 42, delete "can be can be applied" and replace with -- can be applied --.
Line 46, delete "to location" and replace with -- to the location --.
Line 56, delete "of location" and replace with -- of the location --.

Column 11,
Line 9, delete "linearly proportion" and replace with -- linearly proportional --.

Signed and Sealed this

Twenty-eighth Day of March, 2006

JON W. DUDAS
*Director of the United States Patent and Trademark Office*